United States Patent
Roh

(10) Patent No.: US 10,556,335 B2
(45) Date of Patent: Feb. 11, 2020

(54) WEARABLE ROBOT AND METHOD FOR CONTROLLING THE SAME

(71) Applicant: Samsung Electronics Co., Ltd., Suwon-Si, Gyeonggi-Do (KR)

(72) Inventor: Chang Hyun Roh, Seoul (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 657 days.

(21) Appl. No.: 14/476,229

(22) Filed: Sep. 3, 2014

(65) Prior Publication Data
US 2015/0134080 A1 May 14, 2015

(30) Foreign Application Priority Data
Nov. 14, 2013 (KR) .................... 10-2013-0138581

(51) Int. Cl.
*B25J 9/00* (2006.01)
*A61H 3/00* (2006.01)
(Continued)

(52) U.S. Cl.
CPC ......... *B25J 9/0006* (2013.01); *A61B 5/04888* (2013.01); *B25J 9/1694* (2013.01);
(Continued)

(58) Field of Classification Search
CPC ... B25J 9/0006; B25J 9/1694; A61B 5/04888; A61B 5/112; A61B 5/1071; A61H 2230/605; A61H 2201/5069; A61H 2201/165; A61H 2201/5079; A61H 2201/5092; A61H 2201/0107; A61H 1/024; A61H 2201/5084; A61H 1/0266;
(Continued)

(56) References Cited

U.S. PATENT DOCUMENTS

| 5,112,296 | A | * | 5/1992 | Beard | A61F 5/0113 128/905 |
| 7,652,386 | B2 | * | 1/2010 | Donelan | F03G 5/00 290/1 R |

(Continued)

FOREIGN PATENT DOCUMENTS

| KR | 20120064571 | A | 6/2012 | |
| KR | 101323019 | B1 | 10/2013 | |
| WO | WO 2008032967 | A1 * | 3/2008 | ............. A61H 3/008 |

OTHER PUBLICATIONS

Ryan Farris, "Performanc Evaluation of a Lower Limb Exoskeleton for Stair Ascent and Descent with Paraplegia", 2012, Conf Proc IEEE Eng Med Siol Soc. 2012; 2012: 1908-1911.*

(Continued)

*Primary Examiner* — Tu A Vo
(74) *Attorney, Agent, or Firm* — Harness, Dickey and Pierce, P.L.C.

(57) ABSTRACT

A wearable robot may include a gear part having an exoskeleton structure to be worn on legs of a user, a sensor part including a first electromyogram (EMG) sensor attached at a first location of at least one leg of the user, and a second EMG sensor attached at a second location, and a controller to detect a walking assist starting point to assist the user with walking, based on a first EMG signal detected by the first EMG sensor and a second EMG signal detected by the second EMG sensor.

14 Claims, 12 Drawing Sheets

(51) Int. Cl.
  *A61B 5/0488* (2006.01)
  *B25J 9/16* (2006.01)
  *A61B 5/107* (2006.01)
  *A61B 5/11* (2006.01)
  *A61H 1/02* (2006.01)

(52) U.S. Cl.
  CPC ............. *A61B 5/1071* (2013.01); *A61B 5/112* (2013.01); *A61H 1/024* (2013.01); *A61H 1/0244* (2013.01); *A61H 1/0266* (2013.01); *A61H 3/00* (2013.01); *A61H 2003/007* (2013.01); *A61H 2201/0107* (2013.01); *A61H 2201/165* (2013.01); *A61H 2201/5058* (2013.01); *A61H 2201/5069* (2013.01); *A61H 2201/5079* (2013.01); *A61H 2201/5084* (2013.01); *A61H 2201/5092* (2013.01); *A61H 2201/5097* (2013.01); *A61H 2230/605* (2013.01); *Y10S 901/01* (2013.01)

(58) Field of Classification Search
  CPC .......... A61H 2201/5097; A61H 1/0244; A61H 2201/5058; A61H 3/00; A61H 2003/007; A61H 1/001; A61H 2001/0211; A61H 1/0262; A61H 2203/0406; A61H 2230/08; A61H 2230/085; A61H 2230/10; A61H 2230/105; Y10S 901/01
  See application file for complete search history.

(56) References Cited

U.S. PATENT DOCUMENTS

| | | | | |
|---|---|---|---|---|
| 7,857,774 | B2* | 12/2010 | Sankai | A61H 3/008 601/35 |
| 2004/0167641 | A1* | 8/2004 | Kawai | A61B 5/1038 700/63 |
| 2005/0130815 | A1* | 6/2005 | Abdoli-Eramaki | A61F 5/026 482/121 |
| 2006/0046907 | A1* | 3/2006 | Rastegar | A61H 3/00 482/91 |
| 2006/0046908 | A1* | 3/2006 | Rastegar | A61H 3/00 482/91 |
| 2006/0046909 | A1* | 3/2006 | Rastegar | A63B 69/0028 482/91 |
| 2006/0046910 | A1* | 3/2006 | Rastegar | A61H 3/00 482/91 |
| 2006/0211956 | A1* | 9/2006 | Sankai | A61B 5/04888 601/5 |
| 2010/0094188 | A1* | 4/2010 | Goffer | A61H 3/008 602/23 |
| 2010/0113980 | A1* | 5/2010 | Herr | A61F 2/60 600/587 |
| 2010/0121232 | A1* | 5/2010 | Sankai | A61H 3/008 601/23 |
| 2010/0125229 | A1* | 5/2010 | Rudolph | A61B 5/1038 602/16 |
| 2010/0256537 | A1* | 10/2010 | Menga | B25J 9/0006 601/34 |
| 2010/0271051 | A1* | 10/2010 | Sankai | A61B 5/1038 324/679 |
| 2010/0324699 | A1* | 12/2010 | Herr | A61F 2/66 623/27 |
| 2011/0066088 | A1* | 3/2011 | Little | B25J 9/0006 601/35 |
| 2011/0166491 | A1* | 7/2011 | Sankai | A41D 13/1281 601/84 |
| 2011/0184225 | A1* | 7/2011 | Whitall | A63B 24/0003 600/28 |
| 2012/0259431 | A1* | 10/2012 | Han | A61F 5/0125 623/24 |
| 2012/0316476 | A1 | 12/2012 | Shimizu et al. | |
| 2013/0289452 | A1* | 10/2013 | Smith | B25J 9/0006 601/33 |
| 2013/0296746 | A1* | 11/2013 | Herr | A61H 3/00 601/34 |
| 2014/0012164 | A1* | 1/2014 | Tanaka | B25J 9/0006 601/35 |
| 2014/0100492 | A1* | 4/2014 | Nagasaka | A61H 3/061 601/34 |

OTHER PUBLICATIONS

Daniel P. Ferris, "An improved powered ankle-foot orthosis using proportional myelectric control", Elsevier, May 1, 2005.*
Winter D. et al. "EMG profiles during normal human walking: stride-to-stride and inter-subject variability" Electroencephalography and clinical Neurophysiology, 1987, 67: p. 402-411.
Korean Office Action dated Jul. 22, 2019 for KR Application No. 10-2013-0138581.

* cited by examiner

WEARABLE ROBOT AND METHOD FOR CONTROLLING THE SAME

CROSS-REFERENCE TO RELATED APPLICATION

This application claims the benefit of Korean Patent Application No. 10-2013-0138581, filed on Nov. 14, 2013 in the Korean Intellectual Property Office, the disclosure of which is incorporated herein by reference.

BACKGROUND

1. Field

Example embodiments relate to a wearable robot capable of detecting a walking assist starting point with minimum use of sensors, and a method for controlling the same.

2. Description of the Related Art

Currently, research is being actively conducted into wearable robots for a variety of applications, for example, enhancement of muscular power of disabled or elderly people to assist them with walking, rehabilitation treatment for people having diseases, and lifting and carrying of heavy loads for soldiers or industrial workers.

In general, wearable robots to enhance muscular power may include an upper-limb power-assist robot and a lower-limb power-assist robot. The lower-limb power-assist robot may be a robot which assists a user with walking by enhancing power of legs of the user. The lower-limb power-assist robot may be driven to sense a walking state of the user and to enhance muscular power according to the walking state.

SUMMARY

Therefore, some example embodiments relate to a wearable robot capable of detecting a walking assist starting point with less sensors, and a method for controlling the same.

Additional example embodiments will be set forth in part in the description which follows and, in part, will be obvious from the description, or may be learned by practice thereof.

In some example embodiments, the wearable robot includes an assistance device having an exoskeleton structure configured to be worn on legs of a user; sensors including a first electromyogram (EMG) sensor and a second EMG sensor, the first EMG sensor configured to attach at a first location on at least one leg of the user and to detect a first EMG signal, the second EMG sensor configured to attach at a second location on the at least one leg and to detect a second EMG signal; and a controller configured to detect a walking assist starting point based on the first EMG signal and the second EMG signal, the walking assist starting point being a point in a walking cycle in which the assistance device assists the user with walking.

In some example embodiments, the first location on the at least one leg of the user corresponds to a location of a tibialis anterior muscle of the user, and the second location of the at least one leg of the user corresponds to a location of a triceps surae muscle of the user.

In some example embodiments, the second location on the at least one leg of the user corresponds to a location of a soleus muscle of the user.

In some example embodiments, the controller is configured to determine the walking assist starting point by detecting when the first EMG signal is in an offset state and the second EMG signal is in an onset state, the onset state being a state when a muscle at the first location is activated and the offset state being a state when a muscle at the second location is deactivated.

In some example embodiments, the controller is configured to determine if an amplitude of each of the first and second EMG signals are above or below a boundary before determining the walking assist starting point.

In some example embodiments, the controller includes a first filter configured to filter each of the first and second EMG signals before determining the walking assist starting point; and a second filter configured to filter each of the first and second EMG signals before determining the walking assist starting point, the second filter having a cutoff frequency different from a cutoff frequency associated with the first filter.

In some example embodiments, the first filter is a low pass filter (LPF), and the second filter has a cutoff frequency associated therewith that is lower than the cutoff frequency associated with the first filter.

In some example embodiments, the sensors further include at least one of a gyro sensor and an acceleration sensor, the gyro sensor configured to detect inclination of an upper body of the user, and the acceleration sensor configured to detect walking acceleration of the user.

In some example embodiments, the controller is configured to calculate a torque to apply to a driver such that the driver assists a muscular power of the user.

In some example embodiments, the controller is configured to calculate the torque such that the torque is proportional to inclination of a body of the user or walking speed of the user.

In some example embodiments, the controller is configured to apply the torque to a driver associated with the assistance device such that the torque is applied for a walking assist duration, the walking assist duration determined based on the walking assist starting point.

In some example embodiments, the walking assist duration is a fixed time beginning from the walking assist starting point.

In some example embodiments, the walking assist duration is from the walking assist starting point until when a foot of a leg different from the at least one leg of the user contacts ground.

In some example embodiments, the driver includes a first driver in a left hip joint of the assistance device, and a second driver in a right hip joint of the assistance device.

In some example embodiments, the controller is configured to, apply the torque to drivers associated with the at least one leg in a direction opposite to a walking direction of the user, and apply the torque to drivers associated with a leg different from to the at least one leg in the walking direction of the user.

Some example embodiments relate to a method for controlling a wearable robot an assistance device having an exoskeleton structure configured to be worn on legs of a user.

In some example embodiments, the method includes receiving a first electromyogram (EMG) signal and a second EMG signal from a first EMG sensor and a second EMG sensor, respectively, the first EMG sensor configured to attach at a first location of at least one leg of the user, the second EMG sensor configured to attach at a second location of the at least one leg; detecting a walking assist starting point based on the first and second EMG signals, the walking assist starting point being a point in a walking cycle in which the assistance device assists the user with walking; calculating a torque to assist a muscular power of the user;

and providing the torque to a driver included in the assistance device such that the assistance device assists the muscular power of the user.

In some example embodiments, the first location on the at least one leg of the user corresponds to a location of a tibialis anterior muscle of the user, and the second location on the at least one leg of the user corresponds to a location of a soleus muscle of the user.

In some example embodiments, the detecting of the walking assist starting point includes detecting when the first EMG signal is in an offset state and the second EMG signal is in an onset state, the onset state being a state when a muscle at the first location is activated and the offset state being a state when a muscle at the second location is deactivated.

In some example embodiments, the driver includes a first driver in a left hip joint of the assistance device, and a second driver in a right hip joint of the assistance device.

In some example embodiments, the applying the torque includes applying the torque to the drivers associated with the at least one leg in a direction opposite to a walking direction of the user; and applying the torque to the driver associated with a leg different from the at least one leg in the walking direction of the user.

BRIEF DESCRIPTION OF THE DRAWINGS

These and/or other example embodiments will become apparent and more readily appreciated from the following description of the embodiments, taken in conjunction with the accompanying drawings of which.

DETAILED DESCRIPTION

Figure 1:
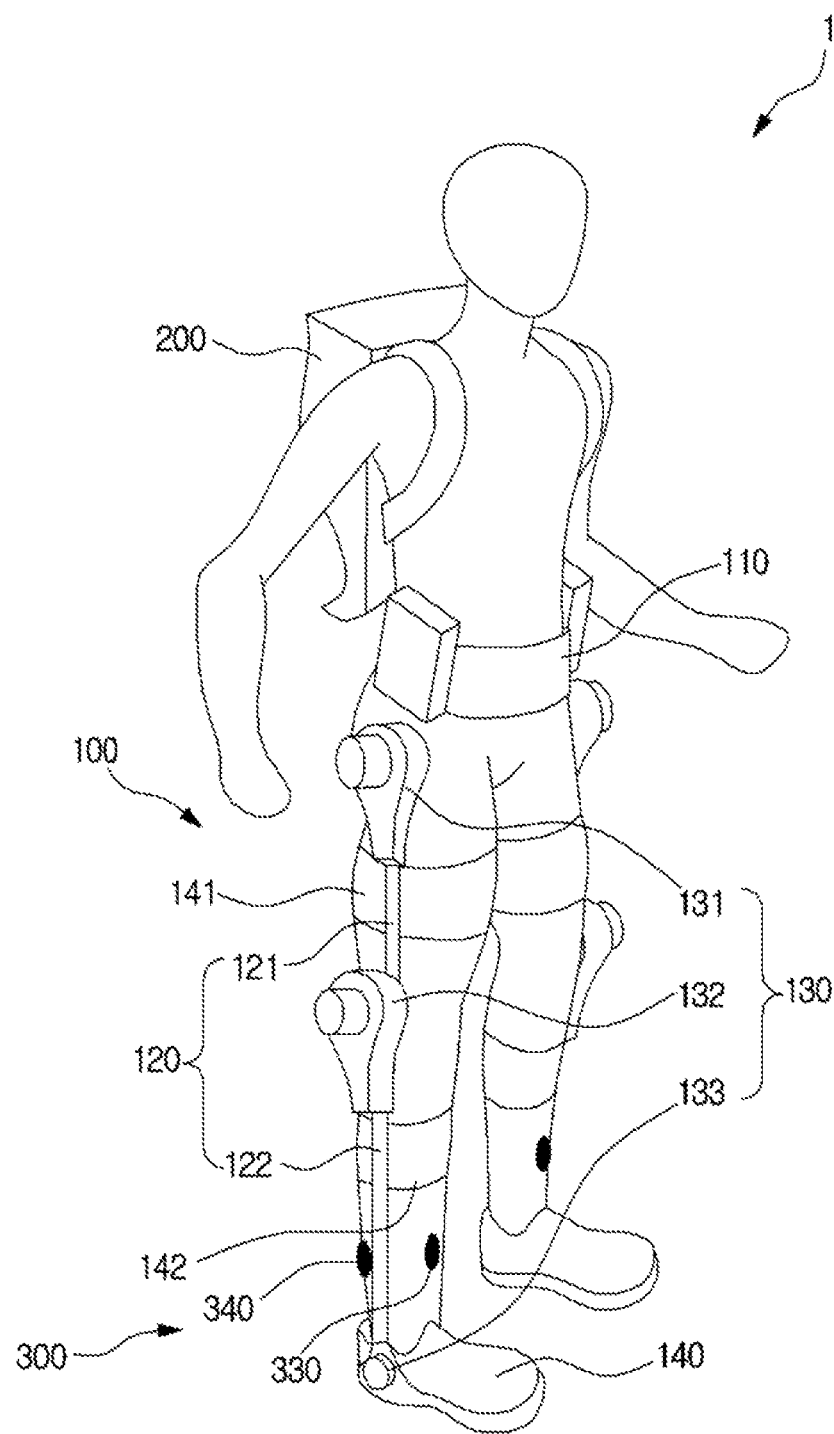
FIG. 1 is an external view of a wearable robot according to some example embodiments.

Reference will now be made in detail to some example embodiments, examples of which are illustrated in the accompanying drawings. The example embodiments may, however, be embodied in many different forms and should not be construed as limited to the example embodiments set forth herein; rather, these example embodiments are provided so that this disclosure will be thorough and complete, and will fully convey the scope of the invention to those skilled in the art.

In the drawings, like reference numerals denote like elements.

Detailed illustrative embodiments are disclosed herein. However, specific structural and functional details disclosed herein are merely representative for purposes of describing example embodiments. Example embodiments may be embodied in many alternate forms and should not be construed as limited to only those set forth herein.

It should be understood, however, that there is no intent to limit this disclosure to the particular example embodiments disclosed. On the contrary, example embodiments are to cover all modifications, equivalents, and alternatives falling within the scope of the example embodiments. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of this disclosure. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting. As used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Various example embodiments will now be described more fully with reference to the accompanying drawings in which some example embodiments are shown. In the drawings, the thicknesses of layers and regions are exaggerated for clarity.

FIG. 1 is an external view of a wearable robot according to some example embodiments.

Referring to FIG. 1, a wearable robot 1 may have an exoskeleton structure to be worn on the legs of a user. The user may perform operations such as extension, flexion, adduction, and abduction while wearing the wearable robot 1. Extension refers to motion of straightening a joint, and flexion refers to motion of bending a joint. Adduction refers to motion of putting a leg close to the central axis of the body, and abduction refers to motion of putting a leg away from the central axis of the body. The wearable robot 1 may include a gear part 100, a controller 200, and a sensor part 300.

The gear part 100 is a part to assist the user with walking. The gear part 100 may include a waist gear 110, a link part 120, a joint part 130, and a foot gear 140.

The waist gear 110 is a part worn on the waist of the user. Although not specifically shown in FIG. 1, the waist gear 110 may include a support pad to support the waist of the user and a fixing part connected to the support pad to surround the stomach of the user.

A cushion may be formed on a part of the support pad contacting the waist of the user. If a cushion is formed on the support pad as described above, wearing sensation may be improved regardless of the shape of the waist of the user.

The fixing part may be formed as a band or belt. The fixing part may be formed of an elastic material. If the fixing part is formed of an elastic material as described above, the user may wear the waist gear 110 regardless of the size of the waist of the user.

The link part 120 supports a leg of the user. The link part 120 may be formed on an outer side of each of left and right legs of the user. The link part 120 supporting one leg has a structure corresponding to that supporting the other leg. The link part 120 may include a first link 121 and a second link 122.

The first link 121 supports an upper leg of the user. The first link 121 may have, for example, a bar shape. One end of the first link 121 is connected to the waist gear 110, and another end of the first link 121 is connected to one end of the second link 122. The first link 121 may have an adjustable length such that the user may adjust the length of the first link 121 to match the length of the upper leg before or after wearing the gear part 100.

The first link 121 may include a fixing part 141. The fixing part 141 fixes the first link 121 to the upper leg of the user. The fixing part 141 may be formed as, for example, a band or belt. The fixing part 141 may be formed of an elastic material. If the fixing part 141 is formed of an inelastic material, the fixing part 141 may have a sufficient length to surround the upper leg regardless of the size of the upper leg of the user.

The second link 122 supports a lower leg of the user. The second link 122 may have, for example, a bar shape. The one end of the second link 122 is connected to the other end of the first link 121. The second link 122 may have an adjustable length such that the user may adjust the length of the second link 122 to match the length of the lower leg before or after wearing the gear part 100.

The second link 122 may include a fixing part 142. The fixing part 142 fixes the second link 122 to the lower leg of the user. The fixing part 142 may be formed as, for example, a band or belt. The fixing part 142 may be formed as an elastic material. If the fixing part 142 is formed of an inelastic material, the fixing part 142 may have a sufficient length to surround the lower leg regardless of the size of the lower leg of the user.

Another end of the second link 122 is connected to the foot gear 140. The foot gear 140 may include a fixing part (not shown) to fix the foot gear 140 to a foot of the user. The fixing part may be formed as a band or belt to surround a top side of the foot of the user.

The joint part 130 may include a hip joint 131, a knee joint 132, and an ankle joint 133. Each of the hip, knee, and ankle joints 131, 132, and 133 may have at least one degree of freedom (DOF). Here, the DOF refers to DOF in forward kinematics or inverse kinematics. DOFs of a figure refer to the number of independent movements of the figure, or the number of parameters to determine independent movement at relative positions of links. For example, an object in a three-dimensional space formed of x, y, and z axes has 3 DOFs to determine the spatial position of the object (i.e., the position on each axis), and 3 DOFs to determine the spatial orientation of the object. In detail, if an object is movable along and rotatable about each axis, the object may be understood as having 6 DOFs.

The hip joint 131 is formed where the one end of the first link 121 is connected to the waist gear 110. The hip joint 131 may be formed to perform at least one of, for example, flexion, extension, adduction, and abduction. The hip joint 131 may be formed as, for example, a revolute joint to rotate about a designated axis.

The knee joint 132 is formed where the first link 121 is connected to the second link 122. The knee joint 132 may be formed to perform flexion and extension. For example, the knee joint 132 may be formed as, for example, a revolute joint.

The ankle joint 133 is formed where the second link 122 is connected to the foot gear 140. The ankle joint 133 may be formed to perform flexion and extension. The ankle joint 133 may be formed as, for example, a revolute joint.

Figure 5:
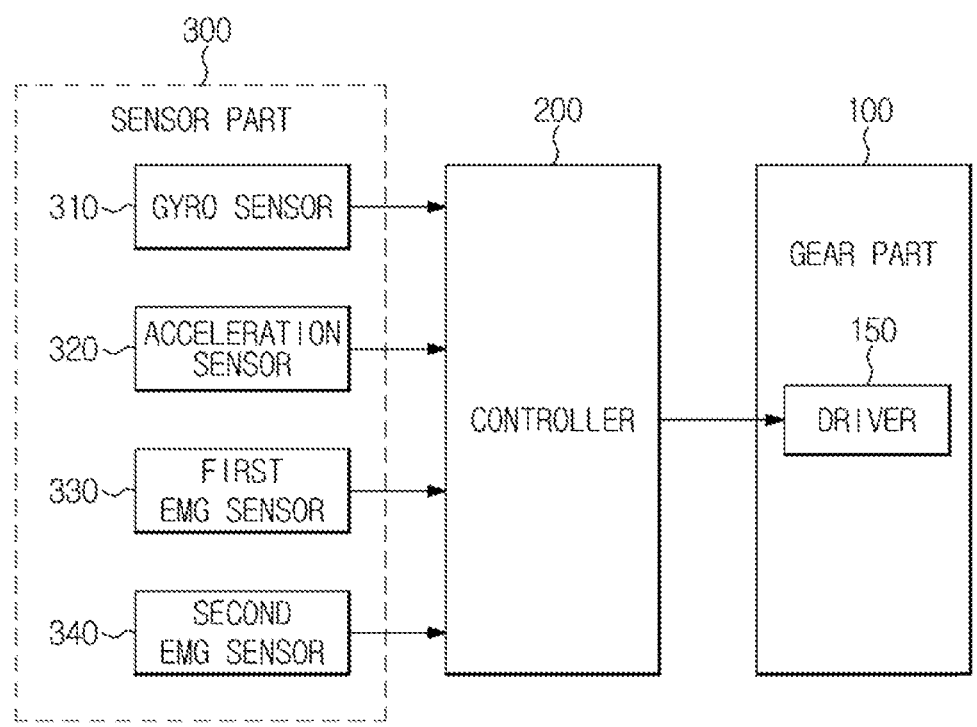
FIG. 5 is a block diagram illustrating the configuration of a wearable robot according to some example embodiments.

Each of the hip, knee, and ankle joints 131, 132, and 133 may include a driver 150 (see FIG. 5). The driver 150 provides driving force to the corresponding hip, knee, or ankle joint 131, 132, or 133 according to a control signal provided from the controller 200. Consequently, the user may be assisted with walking. The driver 150 may be formed as one of, for example, a motor, a vacuum pump, and a hydraulic pump, but the driver 150 is not limited thereto.

The sensor part 300 may measure a physical quantity required to determine a walking state of the user, for example, sound, light, temperature, pressure, acceleration, speed, or inclination. A signal measured by the sensor part 300 may be transmitted to the controller 200. For example, the signal output from the sensor part 300 may be transmitted to the controller 200 using wired or wireless communication. As illustrated in more detail in FIG. 5, the sensor part 300 may include, for example, a gyro sensor 310, an acceleration sensor 320, and an electromyogram (EMG) sensor 330 and 340.

The gyro sensor 310 may measure the inclination of the upper body of the user. The gyro sensor 310 may be, for example, a triaxial gyro sensor. The gyro sensor 310 may be mounted on, for example, the waist gear 110. For example, the gyro sensor 310 may be mounted at a location of the waist gear 110 corresponding to the upper body of the user.

The acceleration sensor 320 may measure acceleration of the user who is walking, or impact received by the user. The acceleration sensor 320 may be, for example, a triaxial acceleration sensor. The acceleration sensor 320 may be mounted on, for example, the waist gear 110. For example, the acceleration sensor 320 may be mounted at a location of the waist gear 110 corresponding to the upper body or pelvis of the user.

The EMG sensor 330 and 340 may be attached to the skin of the user and may measure an EMG signal. The EMG signal is a biological signal representing the state of a muscle. For example, the EMG signal may be a signal obtained by sensing, using an electrode, a small potential difference that occurs in muscle fibers when a muscle is contracted. The EMG signal may be measured by sticking a pin into a muscle of the user or by attaching an electrode to the skin of the user. Hereinafter, it is assumed that the EMG sensor 330 and 340 measures an EMG signal by attaching an electrode to the skin of the user.

According to some example embodiments, the EMG sensor 330 and 340 may include a first EMG sensor 330 and a second EMG sensor 340. The first and second EMG sensors 330 and 340 may be attached to the lower leg of the user. For example, the first EMG sensor 330 may be attached to the tibialis anterior of the user. The second EMG sensor 340 may be attached to the soleus of the triceps surae muscle that forms the calf at a rear part of the lower leg of the user.

If the first and second EMG sensors 330 and 340 are attached at the above-described locations, compared to a case that the first and second EMG sensors 330 and 340 are attached to the upper leg of the user, discomfort may be reduced. In addition, if a walking assist starting point is detected based on an EMG signal detected by the first EMG sensor 330 and an EMG signal detected by the second EMG sensor 340, more reliable results may be obtained. Reasons for determining locations at which the first and second EMG sensors 330 and 340 are attached will be described in detail below with reference to FIGS. 3 and 4.

Meanwhile, the first and second EMG sensors 330 and 340 may be formed separately in hardware. In this case, the user may manually attach or detach the first and second EMG sensors 330 and 340 at or from designated locations.

Alternatively, the first and second EMG sensors 330 and 340 may be formed separately in hardware, and may be embedded in, for example, socks or stockings surrounding lower legs. In this case, the user may simply wear socks or stockings to achieve the effect of attaching the first and second EMG sensors 330 and 340 to corresponding parts.

The above-described first and second EMG sensors 330 and 340 may be attached to each of two legs of the user. That is, the first and second EMG sensors 330 and 340 are attached at designated locations of the left leg of the user, and are also attached at designated locations of the right leg of the user.

Each of the gyro sensor 310, the acceleration sensor 320, and the first and second EMG sensors 330 and 340 included in the sensor part 300 may be formed as separate hardware. However, all sensors are not limited to separate hardware, and one sensor may be integrated with another sensor. For example, the acceleration sensor 320 may be integrated with the gyro sensor 310. As another example, the acceleration sensor 320 may be integrated with the first and second EMG sensors 330 and 340.

Figure 2B:
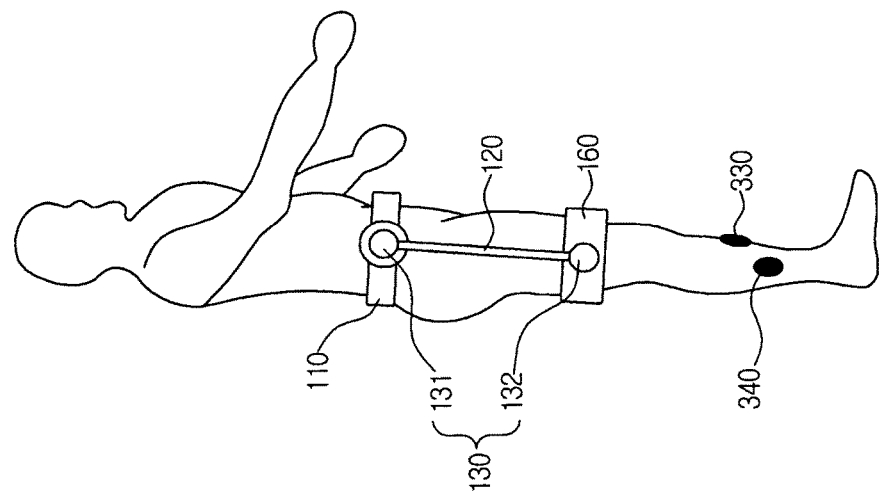
FIG. 2 is an external view of a wearable robot according to other example embodiments.
Figure 2A:
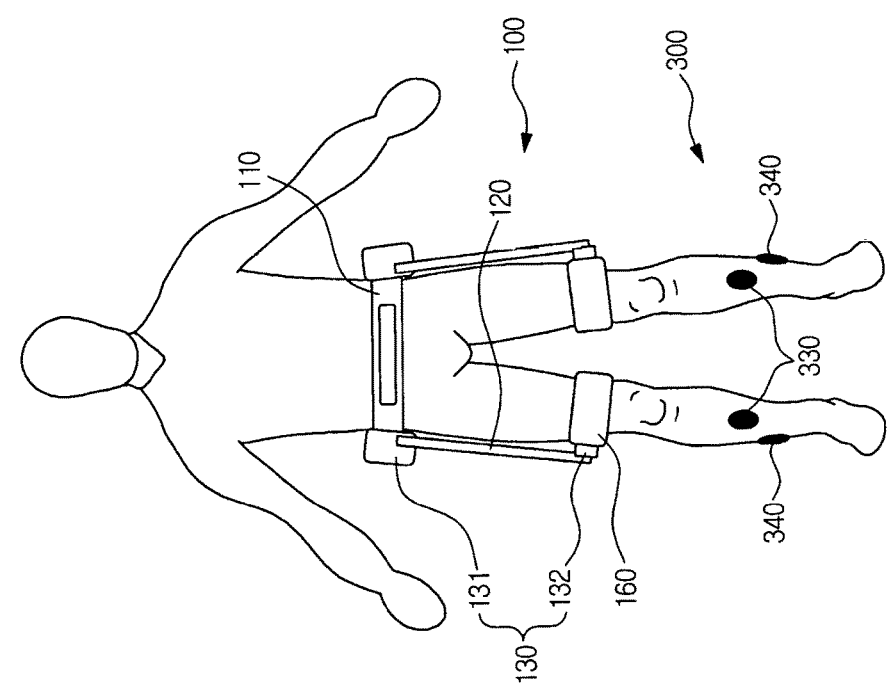

FIG. 2 is an external view of a wearable robot 10 according to other example embodiments.

Referring to FIG. 2, a wearable robot 10 may assist only upper legs of the user, by, for example, slight modification of the wearable robot 1 of FIG. 1 which may assist both upper and lower legs of the user while the user is walking.

The wearable robot 10 may include a gear part 100, a sensor part 300, and a controller (not shown). The sensor part 300 and the controller of FIG. 2 may be the same as or similar to the sensor part 300 and the controller 200 of FIG. 1, therefore, repeated descriptions thereof will be omitted herein for the sake of brevity and the gear part 100 will be focused upon.

The gear part 100 is a part to enhance muscular power of upper legs of a user while the user is walking. The gear part 100 may include a waist gear 110, an upper leg gear 160, a link part 120, and a joint part 130.

The waist gear 110 is a part worn on the waist of the user. Although not specifically shown in FIG. 2, the waist gear 110 may include a support pad to support the waist of the user and a fixing part connected to the support pad to surround the stomach of the user. The fixing part may be formed as a band or belt.

The upper leg gear 160 is a part worn on the upper leg of the user. The upper leg gear 160 may be formed on each of left and right upper legs of the user. Although not specifically shown in FIG. 2, the upper leg gear 160 may include a support pad to support the upper leg of the user, for example, a part immediately above the knee, and a fixing part connected to the support pad to surround the upper leg of the user. The fixing part may be formed as a band or belt.

The link part 120 supports the upper leg of the user. The link part 120 may be formed on each of left and right upper legs of the user. Although not specifically shown in FIG. 2, the link part 120 may have a bar shape. One end of the link part 120 is connected to the waist gear 110, and another end of the link part 120 is connected to the upper leg gear 160. The link part 120 may have an adjustable length such that the user may adjust the length of the link part 120 to match the length of the upper leg before or after wearing the gear part 100.

The joint part 130 may include a hip joint 131 and a knee joint 132. Each of the hip and knee joints 131 and 132 may have at least one DOF. The hip joint 131 is formed where the one end of the link part 120 is connected to the waist gear 110. The hip joint 131 may be formed to perform at least one of, for example, flexion, extension, adduction, and abduction. The knee joint 132 is formed where the other end of the link part 120 is connected to the upper leg gear 160. The knee joint 132 may be formed to perform, for example, flexion and extension. In this regard, the knee joint 132 may be formed as, for example, a revolute joint.

Each of the hip and knee joints 131 and 132 may include a driver 150 (see FIG. 5). The driver 150 provides driving force to the corresponding hip or knee joint 131 or 132 according to a control signal provided from the controller. The driver may be formed as one of, for example, a motor, a vacuum pump, and a hydraulic pump, but is not limited thereto.

Figure 3:
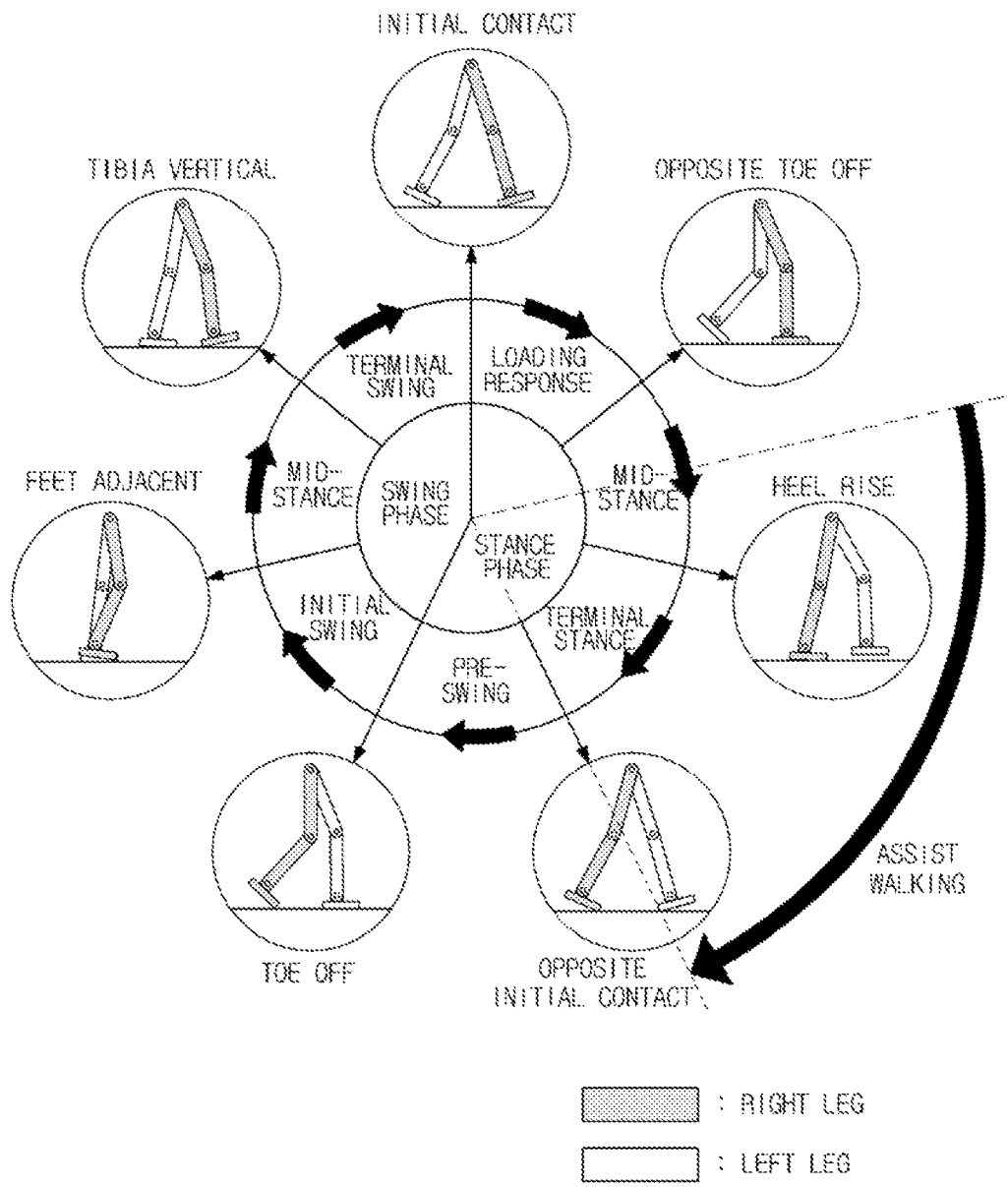
FIG. 3 is a view illustrating a single gait cycle of human walking.
Figure 4:
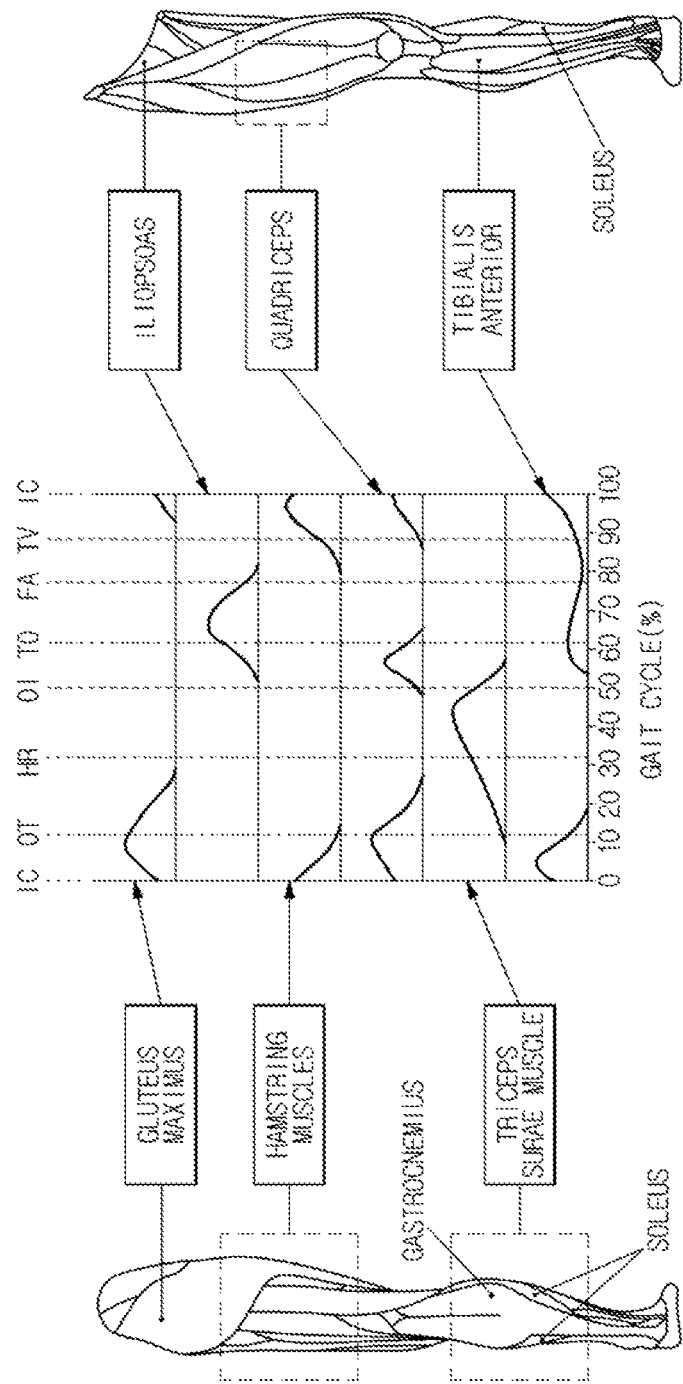
FIG. 4 is a view illustrating activities of major muscle groups in the single gait cycle and anatomical locations of the major muscle groups.

FIG. 3 is a view illustrating a single gait cycle of human walking. FIG. 4 is a view illustrating typical activities of major muscle groups in the single gait cycle and anatomical locations of the major muscle groups.

Referring to FIGS. 3 and 4, the locations at which the first and second EMG sensors 330 and 340 are attached to a user may be determined based on a gait cycle of the user.

A gait cycle refers to a cycle from when a heel of one leg contacts the ground until when the heel of the same leg contacts the ground again. FIG. 3 illustrates a gait cycle of a right leg. A gait cycle will now be described based on a right leg.

The gait cycle is divided into seven (7) periods that may be classified as part of a stance phase or a swing phase. The stance phase refers to a period in which the right leg contacts the ground to support the weight, and normally occupies 60% of the gait cycle. The swing phase refers to a period in which the right leg is separated from the ground, and normally occupies 40% of the gait cycle.

The stance phase is divided into loading response, mid-stance, terminal stance, and pre-swing periods. The swing phase is divided into initial swing, mid-stance, and terminal swing.

In order to divide the gait cycle into the 7 periods described above, walking is divided into 8 operations, for example, initial contact IC, opposite toe off OT, heel rise HR, opposite initial contact OI, toe off TO, feet adjacent FA, tibia vertical TV, and next initial contact IC.

The initial contact IC refers to when a right foot contacts the ground. The initial contact IC corresponds to 0% point of the gait cycle out of 100%. The initial contact IC corresponds to a starting point of the stance phase.

The opposite toe off TO refers to when left toes are separated from the ground, and corresponds to 10% point of the gait cycle.

The heel rise HR refers to when a right heel is lifted up from the ground, and occurs at 30% point of the gait cycle.

The opposite initial contact OI refers to when a left heel contacts the ground, and occurs at 50% point of the gait cycle.

The toe off TO refers to when right toes are separated from the ground, and occurs at 60% point of the gait cycle.

The feet adjacent FA refers to when a right foot being in the swing phase is next to a left foot being in the stance phase. The feet adjacent FA occurs at 73% point of the gait cycle.

The tibia vertical TV refers to when tibia of the right leg being in the swing phase is in a direction perpendicular to the ground. The tibia vertical TV occurs at 87% point of the gait cycle.

As described above, the stance phase is divided into loading response, mid-stance, terminal stance, and pre-swing periods. The loading response corresponds to a period from the initial contact IC to the opposite toe off OT. The mid-stance corresponds to a period from the opposite toe off OT to the heel rise HR. The terminal stance corresponds to a period from the heel rise HR to the opposite initial contact OI. The pre-swing corresponds to a period from the opposite initial contact OI to the toe off TO.

The swing phase is divided into initial swing, mid-stance, and terminal swing periods. The initial swing corresponds to a period from the toe off TO to the feet adjacent FA. The mid-stance corresponds to a period from the feet adjacent FA to the tibia vertical TV. The terminal swing corresponds to a period from the tibia vertical TV to the next initial contact IC.

Activities of major muscle groups in the gait cycle are illustrated in FIG. 4.

Referring to FIG. 4, the gluteus maximus, iliopsoas, hamstring muscles, quadriceps femoris muscle, triceps surae muscle, and tibialis anterior are shown as the major muscle groups.

As noted in FIG. 4, the hamstring muscles and quadriceps femoris muscle are activated at an initial state of walking. As such, an EMG signal measured at the hamstring muscles or quadriceps femoris muscle may be used as data to determine a walking assist starting point. However, an EMG sensor may not be easily attached to the hamstring muscles or quadriceps femoris muscle, and a user may experience discomfort if the EMG sensor is attached to such a part.

Meanwhile, in FIG. 4, in a period between the opposite toe off OT and the heel rise HR, both the hamstring muscles and quadriceps femoris muscle are activated at a point when the tibialis anterior is deactivated and the triceps surae muscle is activated. Therefore, if EMG signals detected at the tibialis anterior and triceps surae muscle are used, a walking assist starting point may be detected without detecting an EMG signal at the hamstring muscles or quadriceps femoris muscle.

In more detail with reference to the gait cycle of FIG. 3, toes of the right leg are lifted and the tibialis anterior is activated (contracted) in the initial contact IC, and the lifted toes of the right leg are dropped and the tibialis anterior is gradually deactivated (released) after the initial contact IC. Then, the left leg swings and the right leg kicks the ground after the opposite toe off OT, and thus the triceps surae muscle of the right leg is gradually activated (contracted). Therefore, if a time point when the tibialis anterior is deactivated and the triceps surae muscle is activated is detected as a walking assist starting point, initial walking may be detected.

For this reason, the first EMG sensor 330 is attached to the tibialis anterior and the second EMG sensor 340 is attached to the triceps surae muscle. The triceps surae muscle is a muscle that forms the calf at a rear part of a lower leg, and includes two gastrocnemii and one soleus. According to some example embodiments, the second EMG sensor 340 may be attached to the soleus. However, attachment of the second EMG sensor 340 is not limited thereto, for example, the second EMG sensor 340 may be attached to the gastrocnemii.

FIG. 5 is a block diagram illustrating the configuration of the wearable robot 1 according to some example embodiments.

As illustrated in FIG. 5, the wearable robot 1 may include the sensor part 300, the controller 200, and the gear part 100.

The sensor part 300 may include the gyro sensor 310, the acceleration sensor 320, the first EMG sensor 330, and the second EMG sensor 340. The gyro sensor 310 may measure the inclination of the upper body of the user, and the acceleration sensor 320 may measure acceleration, vibration, or impact of the user. The first EMG sensor 330 is attached to the tibialis anterior of the user to detect an EMG signal. The second EMG sensor 340 may be attached to the soleus of the user to detect an EMG signal.

Figure 6:
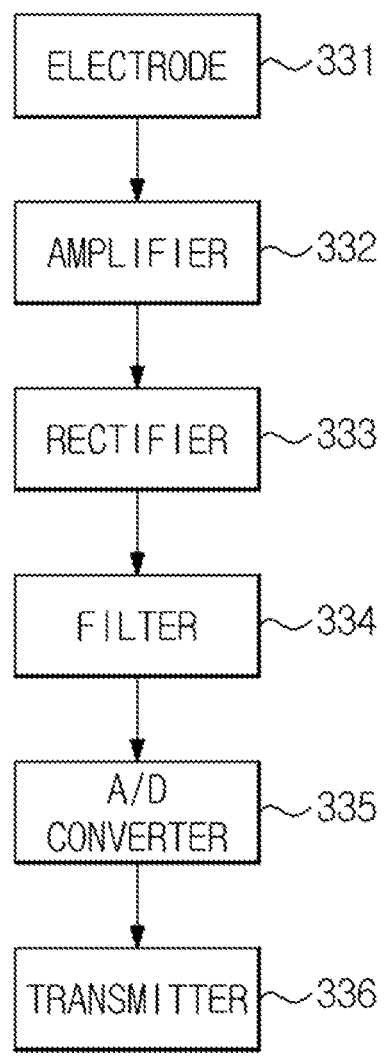
FIG. 6 is a block diagram illustrating the configuration of a first electromyogram (EMG) sensor according to some example embodiments.

FIG. 6 is a block diagram illustrating the configuration of the first EMG sensor 330 according to an embodiment of the present invention.

Referring to FIG. 6, the first and second EMG sensors 330 and 340 may have the same configuration and thus the first EMG sensor 330 will be described representatively.

The first EMG sensor 330 may include an electrode 331, an amplifier 332, a rectifier 333, a filter 334, an analog-to-digital (A/D) converter 335, and a transmitter 336.

The electrode 331 is a part to be attached to the skin of the user, and may include one or more electrodes. For example, the electrode 331 may include a reference electrode (+), an active electrode (−), and a ground electrode. The reference electrode (+) may be attached near a tendon or bone. The active electrode (−) may be attached near a muscle. The ground electrode may be attached to a body. The electrode 331 may be, for example, an Ag/AgCl electrode.

The amplifier 332 may amplify the potential difference formed between the reference electrode and the active electrode, i.e., an EMG signal. The amplifier 332 may amplify the EMG signal at an amplification ratio of 1000:1. However, the amplifier 332 is not limited thereto and may amplify the EMG signal at a different amplification ratio. The EMG signal amplified by the amplifier 332 may be provided to the rectifier 333.

The rectifier 333 may rectify the EMG signal provided from the amplifier 332. The rectifier 333 may rectify the EMG signal by obtaining an absolute value of the EMG signal. Since the EMG signal has both positive and negative values, a value close to 0 is obtained if the positive and negative values are averaged. Since characteristics of the EMG signal may be distorted if the EMG signal is used as it is, the absolute value of the EMG signal is calculated. The rectified EMG signal may be provided to the filter 334.

The filter 334 may filter the EMG signal provided from the rectifier 333. The filter 334 may filter the rectified EMG signal to separate useful information from the EMG signal. For example, the useful information of the EMG signal may be in a range of 10 to 500 Hz. Therefore, if the EMG signal is analog filtered using a high pass filter (HPF) having a cutoff frequency of 10 Hz and a low pass filter (LPF) having a cutoff frequency of 500 Hz, an EMG signal including useful information may be separated from the amplified EMG signal. The EMG signal filtered by the filter 334 may be provided to the A/D converter 335.

The A/D converter 335 may convert the EMG signal provided from the filter 334, from an analog value into a digital value. The digital-converted EMG signal may be provided to the transmitter 336.

The transmitter 336 cooperates with a receiver of the controller 200 to be described below. The transmitter 336 may transmit the digital-converted EMG signal to the controller 200. In this case, the digital-converted EMG signal may be transmitted using wired or wireless communication. If wired communication is used, a special fiber, for example, a conductive fiber, may be formed between the transmitter 336 of the first EMG sensor 330 and the receiver of the controller 200, and the EMG signal may be transmitted using the special fiber. If wireless communication is used between the transmitter 336 of the first EMG sensor 330 and the receiver of the controller 200, the EMG signal may be transmitted using, for example, Bluetooth, ZigBee (IEEE 802.15.1), radio frequency identification (RFID), wideband code division multiple access (WCDMA), or Wi-Fi (by Wi-Fi Alliance).

A signal measured by the first EMG sensor 330 is transmitted to the controller 200 using wired or wireless communication in the above description. However, the above principal is not limited to the first EMG sensor 330, and a signal(s) measured by the gyro sensor 310 and/or the acceleration sensor 320 may also be transmitted to the controller 200 using wired or wireless communication.

Referring back to FIG. 5, the controller 200 may detect a walking assist starting point based on the EMG signal transmitted from the first EMG sensor 330 (hereinafter referred to as 'first EMG signal') and the EMG signal transmitted from the second EMG sensor 340 (hereinafter referred to as 'second EMG signal'). In addition, the controller 200 may generate a control signal to control the driver 150 to assist the muscular power of the user based on at least one of the signals transmitted from the gyro sensor 310 and the acceleration sensor 320. The generated control signal may be transmitted to the driver 150 included in the gear part 100. The configuration of the controller 200 will now be described in detail with reference to FIG. 7.

Figure 7:
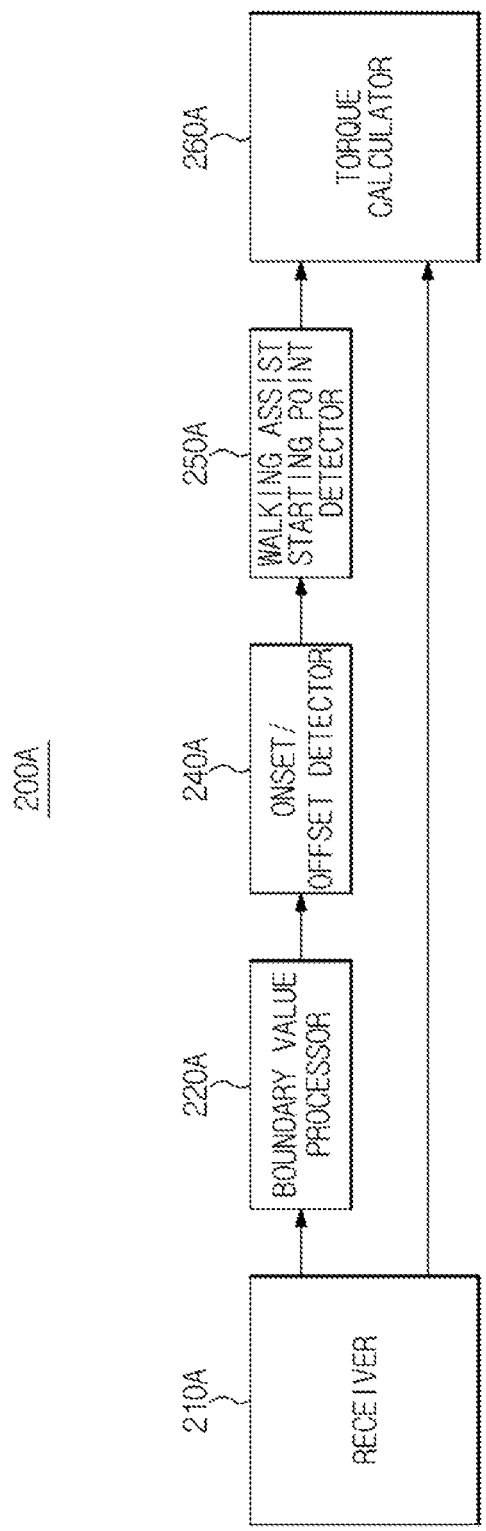
FIG. 7 is a block diagram illustrating the configuration of a controller according to some example embodiments.

FIG. 7 is a block diagram illustrating the configuration of a controller 200A according to some example embodiments.

Referring to FIG. 7, the controller 200A may include a receiver 210A, a boundary value processor 220A, an onset/offset detector 240A, a walking assist starting point detector 250A, and a torque calculator 260A.

The receiver 210A may receive the signals detected by the gyro sensor 310, the acceleration sensor 320, and the first and second EMG sensors 330 and 340 of the sensor part 300. As described above, the signals may be received using wired or wireless communication.

Among the signals received by the receiver 210A, the signal detected by the gyro sensor 310 and/or the acceleration sensor 320 may be provided to the torque calculator 260A to be described below. Further, the first and second EMG signals respectively detected by the first and second EMG sensors 330 and 340 may be provided to the boundary value processor 220A to be described below.

The boundary value processor 220A may perform boundary value processing on each of the first and second EMG signals. The boundary value processor 220A may output one of two signals based on whether an amplitude of the EMG signal is above or below a boundary value. For example, the boundary value processor 220A may output value 1 with respect to an EMG signal having an amplitude equal to or greater than a boundary value, and output value 0 with respect to an EMG signal having an amplitude less than the boundary value. The first and second EMG signals on which boundary value processing is performed may be provided to the onset/offset detector 240A.

The onset/offset detector 240A may detect an onset point and an offset point from the first EMG signal on which boundary value processing is performed. Likewise, the onset/offset detector 240A may detect an onset point and an offset point from the second EMG signal on which boundary value processing is performed. Here, the onset point refers to a time point when a muscle is activated, and the offset point refers to a time point when the muscle is inactivated. The onset point may correspond to a moment when a waveform of an EMG signal on which boundary value processing is performed rises. On the other hand, the offset point may correspond to a moment when a waveform of an EMG signal on which boundary value processing is performed falls. The detection results of the onset/offset detector 240A may be provided to the walking assist starting point detector 250A to be described below.

The walking assist starting point detector 250A may detect a walking assist starting point based on the onset and offset points detected from the first EMG signal and the onset and offset points detected from the second EMG signal.

In detail, the walking assist starting point detector 250A may detect a time point when the first EMG signal is in an offset state and the second EMG signal is in an onset state, as the walking assist starting point. For example, the walking assist starting point detector 250A may detect a time when the first EMG signal, connected to the tricep surae muscle, rises and a time when the second EMG signal, connected to the tibialis anterior muscle, falls.

The walking assist starting point detector 250A may detect the walking assist starting point regardless of whether the offset state of the first EMG signal or the onset state of the second EMG signal occurs first. For example, even when the first EMG signal is offset first and then the second EMG signal is onset, a time point that satisfies the offset state of the first EMG signal and the onset state of the second EMG signal may be detected as the walking assist starting point. As another example, even when the second EMG signal is onset first and then the first EMG signal is offset, a time point that satisfies the offset state of the first EMG signal and the onset state of the second EMG signal may be detected as the walking assist starting point. The result of detecting the walking assist starting point may be provided to the torque calculator 260A to be described below.

The torque calculator 260A may generate torques to apply to the driver 150 to assist muscular power of the user for a walking assist time based on the walking assist starting point.

According to some example embodiments, the walking assist time may refer to a fixed time from the walking assist starting point. For example, the walking assist time may be 2 sec. from the walking assist starting point.

According to other example embodiments, the walking assist time may refer to a time from the walking assist starting point until when the foot of a swing leg contacts the ground. Referring to FIGS. 3 and 4, it is noted that the walking assist starting point for the right leg may be detected while the right leg is a support leg. It is also noted that the left leg swings to contact the ground after the walking assist starting point for the right leg is detected. Therefore, a time from the walking assist starting point until when the foot of the left leg that is a swing leg contacts the ground may be determined as the walking assist time.

Although only the walking assist starting point for the right leg is illustrated in the FIG. 3, the walking assist starting point for the left leg is detected while the left leg is a support leg. That is, the walking assist starting point for the left leg is detected after the toe off TO in FIG. 3. The user may be assisted with walking from when the walking assist starting point for the left leg is detected until when the right leg swings to contact the ground again, i.e., the initial contact IC.

Meanwhile, the torque calculator 260A may calculate torques to be provided to the drivers 150 included in the hip joints 131. The magnitude of the torques to be provided to the drivers 150 included in the hip joints 131 may be proportional to the inclination of the body of the user with respect to the ground or the speed of the user. The inclination of the body of the user with respect to the ground may be detected by the gyro sensor 310. The speed of the user may be calculated based on the acceleration detected by the acceleration sensor 320.

Torques in opposite directions may be provided to the driver 150 included in the hip joint 131 of a support leg and the driver 150 included in the hip joint 131 of a swing leg. In detail, a torque in a direction opposite to a walking direction of the user may be provided to the driver 150 included in the hip joint 131 of a support leg. On the other hand, a torque in the walking direction of the user may be provided to the driver 150 included in the hip joint 131 of a swing leg.

In more detail, referring to FIGS. 3 and 4, it is noted that the walking assist starting point for the right leg is detected after the opposite toe off OT. It is also noted that the heel rise HR is performed after the opposite toe off OT. In the heel rise HR, the user kicks the ground with the right leg and lifts the left leg to take a step forward. That is, the user applies a force in a direction opposite to the walking direction to the right leg, and applies a force in the walking direction to the left leg. Therefore, if the driver 150 provides a torque in a direction opposite to the walking direction to the hip joint 131 of the right leg (support leg) and a torque in the walking direction to the hip joint 131 of the left leg (swing leg), the user may be assisted with walking.

Figure 8:
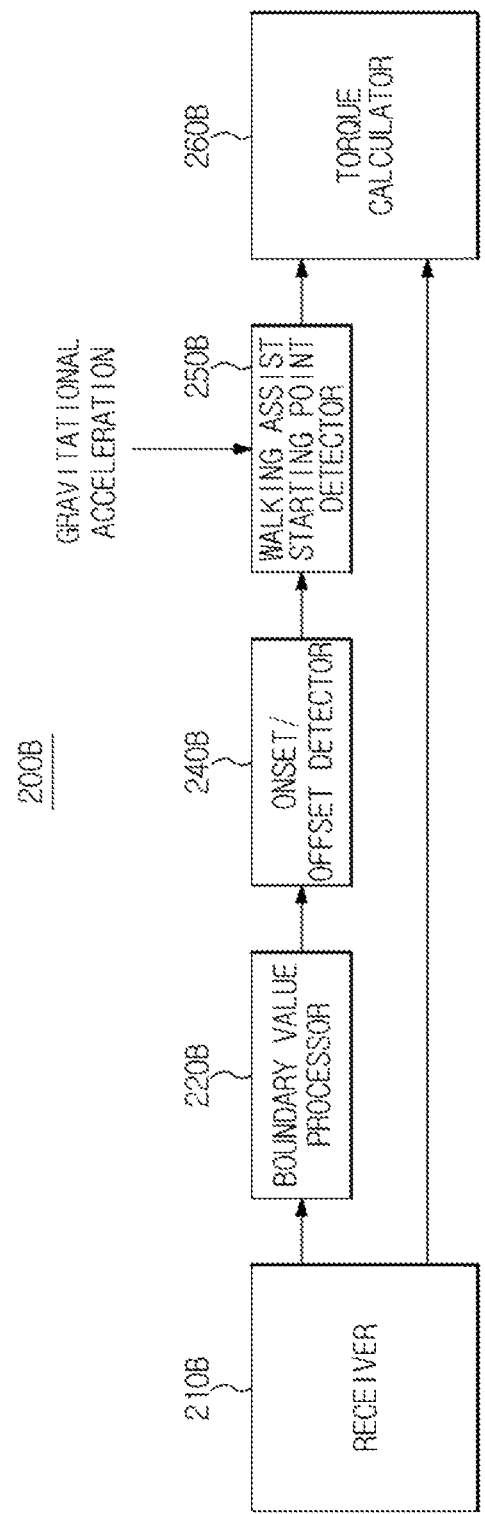
FIG. 8 is a block diagram illustrating the configuration of a controller according to other example embodiments.

FIG. 8 is a block diagram illustrating the configuration of a controller 220B according to other example embodiments.

As illustrated in FIG. 8, the controller 220B may include a receiver 210B, a boundary value processor 220B, an onset/offset detector 240B, a walking assist starting point detector 250B, and a torque calculator 260B.

The receiver 210B, the boundary value processor 220B, the onset/offset detector 240B, and the torque calculator 260B of FIG. 8 may be the same or similar to the receiver 210A, the boundary value processor 220A, the onset/offset detector 240A, and the torque calculator 260A of FIG. 7, therefore, repeated descriptions thereof are omitted herein for the sake of brevity, and the walking assist starting point detector 250B will be described below.

The walking assist starting point detector 250B may detect a walking assist starting point based on the onset and offset points detected from the first EMG signal, the onset and offset points detected from the second EMG signal, and a gravitational acceleration. In detail, the walking assist starting point detector 250B may detect a time point when the first EMG signal is in an offset state and the second EMG signal is in an onset state after the gravitational acceleration is rapidly increased, as the walking assist starting point.

In detail, if a user stands still, the gravitational acceleration measured by the wearable robot 1 is 1 g in a direction perpendicular to the ground. In this state, if the user starts walking and thus the initial contact IC of FIG. 3 is performed, the heel of the right leg contacts the ground and the gravitational acceleration measured by the wearable robot 1 rapidly increases. If the opposite toe off OT is performed after the initial contact IC, the walking assist starting point for the right leg is detected.

As described above, the walking assist starting point is detected after the gravitational acceleration rapidly increases. Therefore, if the gravitational acceleration is used in addition to the first and second EMG signals, the walking assist starting point may be more accurately detected. That is, since an EMG signal may be measured even when the user does not move a leg, the accuracy of the detection based on the EMG signal may be supplemented by the gravitational acceleration measured by the wearable robot 1.

Meanwhile, the walking assist starting point may be detected regardless of whether the offset state of the first EMG signal or the onset state of the second EMG signal occurs first.

For example, after the gravitational acceleration measured by the wearable robot 1 is rapidly increased, even when the first EMG signal is offset first and then the second EMG signal is onset, a time point that satisfies the offset state of the first EMG signal and the onset state of the second EMG signal may be detected as the walking assist starting point. As another example, after the gravitational acceleration measured by the wearable robot 1 is rapidly increased, even when the second EMG signal is onset first and then the first EMG signal is offset, a time point that satisfies the offset state of the first EMG signal and the onset state of the second EMG signal may be detected as the walking assist starting point.

Figure 9:
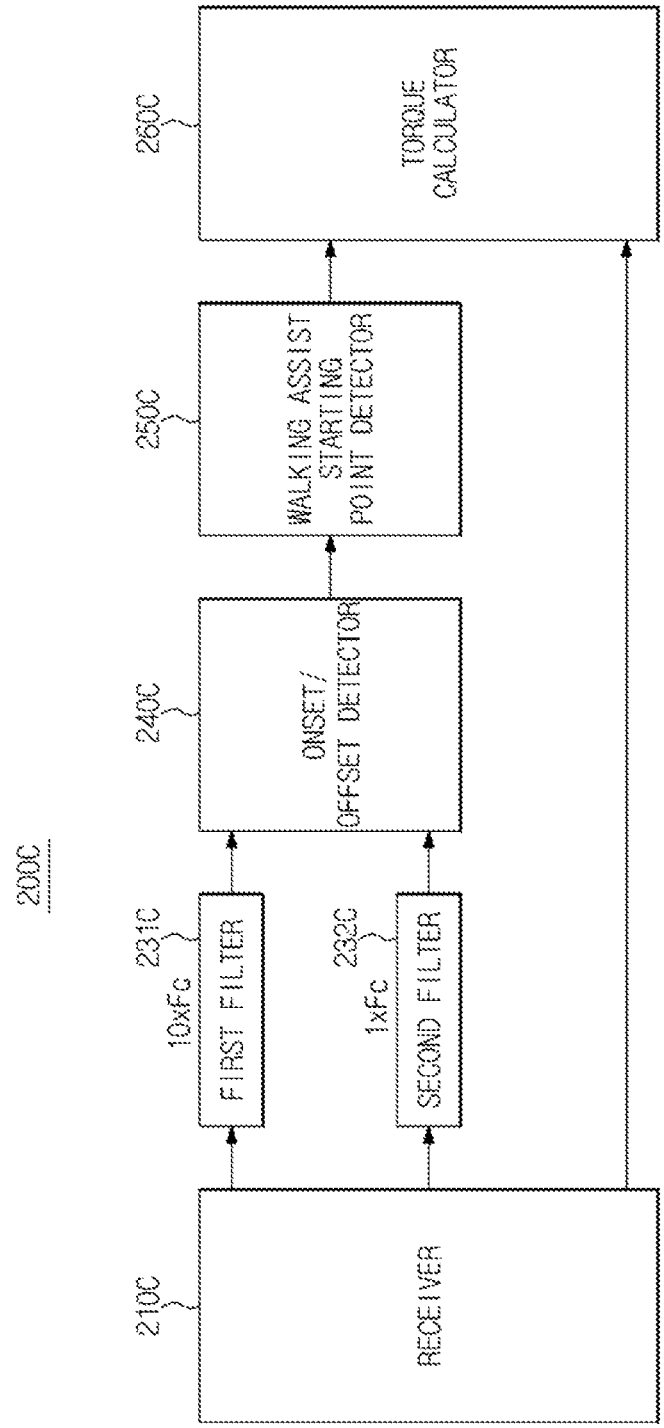
FIG. 9 is a block diagram illustrating the configuration of a controller according to other example embodiments.

FIG. 9 is a block diagram illustrating the configuration of a controller 200C according to other example embodiments.

As illustrated in FIG. 9, the controller 220C may include a receiver 210C, a first filter 231C, a second filter 232C, an onset/offset detector 240C, a walking assist starting point detector 250C, and a torque calculator 260C. As illustrated in FIG. 9, the controller 200C illustrated in FIG. 9 includes a first and second filters 231C and 232C as compared to the controller 200A illustrated in FIG. 7 which includes the boundary value processor 220A.

The receiver 210C may receive signals detected by sensors of the sensor part 300. The signals may be received using wired or wireless communication. Among the signals received by the receiver 210C, the signal detected by the gyro sensor 310 or the acceleration sensor 320 may be provided to the torque calculator 260C. Among the signals received by the receiver 210C, the first and second EMG signals detected by the first and second EMG sensors 330 and 340 may be provided to the first and second filters 231C and 232C to be described below, respectively.

The first and second filters 231C and 232C may be LPFs having different cutoff frequencies. For example, if the second filter 232C has a cutoff frequency of Fc, the first filter 231C may have a cutoff frequency of 10×Fc.

By utilizing the first and second filters 231C and 232C having different cutoff frequencies, the controller 200C may account for situations where an EMG signal may have different levels according to the locations of the first and second EMG sensors 330 and 340, and the sex, age, and condition of a user. Therefore, if LPFs having different cutoff frequencies are used to determine the onset and offset points, instead of boundary value processing, the controller 200C may be more versatile.

The onset/offset detector 240C may subtract the first EMG signal filtered by the second filter 232C from the first EMG signal filtered by the first filter 231C. Consequently, a first EMG signal, a baseline of which is zeroed, i.e., a first EMG signal similar to an actual first EMG signal, is obtained.

Likewise, the onset/offset detector 240C may subtract the second EMG signal filtered by the second filter 232C from the second EMG signal filtered by the first filter 231C. Consequently, a second EMG signal, a baseline of which is zeroed, i.e., a second EMG signal similar to an actual second EMG signal, is obtained.

If the first and second EMG signals, baselines of which are zeroed, are obtained as described above, the onset/offset detector 240C may detect an onset point and an offset point from each of the obtained first and second EMG signals. The onset and offset points detected from the first EMG signal and the onset and offset points detected from the second EMG signal may be provided to the walking assist starting point detector 250C to be described below.

The walking assist starting point detector 250C may detect a walking assist starting point based on the onset and offset points detected from the first EMG signal and the onset and offset points detected from the second EMG signal.

In detail, the walking assist starting point detector 250C may detect a time point when the first EMG signal is in an offset state and the second EMG signal is in an onset state, as the walking assist starting point. In this case, the walking assist starting point may be detected regardless of whether the offset state of the first EMG signal or the onset state of the second EMG signal occurs first.

For example, even when the first EMG signal is offset first and then the second EMG signal is onset, a time point that satisfies the offset state of the first EMG signal and the onset state of the second EMG signal may be detected as the walking assist starting point. As another example, even when the second EMG signal is onset first and then the first EMG signal is offset, a time point that satisfies the offset state of the first EMG signal and the onset state of the second EMG signal may be detected as the walking assist starting point. The result of detecting the walking assist starting point may be provided to the torque calculator 260D to be described below.

The torque calculator 260C may generate torques to apply to the driver 150 to enhance muscular power of the user for a walking assist time based on the walking assist starting point.

Figure 10:
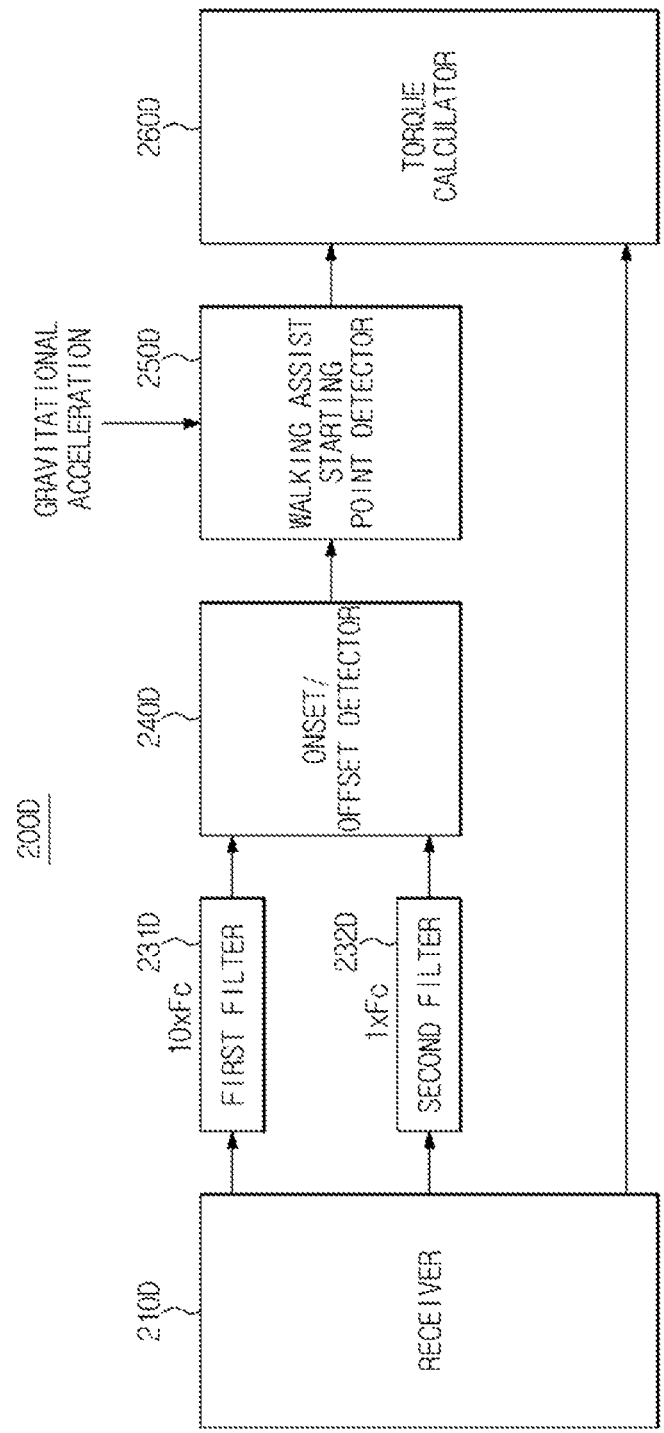
FIG. 10 is a block diagram illustrating the configuration of a controller according to other example embodiments.

FIG. 10 is a block diagram illustrating the configuration of a controller 200D according to other example embodiments.

As illustrated in FIG. 10, the controller 220D may include a receiver 210D, a first filter 231C, a second filter 232C, an onset/offset detector 240D, a walking assist starting point detector 250D, and a torque calculator 260D.

The receiver 210D, the first filter 231D, the second filter 232D, the onset/offset detector 240D, and the torque calculator 260D of FIG. 10 may be the same or similar to the receiver 210C, the first filter 231C, the second filter 232C, the onset/offset detector 240C, and the torque calculator 260C of FIG. 9, therefore, repeated descriptions thereof is omitted herein for the sake of brevity and the walking assist starting point detector 250D is described below.

The walking assist starting point detector 250D may detect a walking assist starting point based on the onset and offset points detected from the first EMG signal, the onset and offset points detected from the second EMG signal, and the gravitational acceleration. In detail, the walking assist starting point detector 250D may detect a time point when the first EMG signal is in an offset state and the second EMG signal is in an onset state after the gravitational acceleration is rapidly increased, as the walking assist starting point.

The walking assist starting point may be detected regardless of whether the offset state of the first EMG signal or the onset state of the second EMG signal occurs first.

For example, after the gravitational acceleration measured by the wearable robot 1 is rapidly increased, even when the first EMG signal is offset first and then the second EMG signal is onset, a time point that satisfies the offset state of the first EMG signal and the onset state of the second EMG signal may be detected as the walking assist starting point. As another example, after the gravitational acceleration measured by the wearable robot 1 is rapidly increased, even when the second EMG signal is onset first and then the first EMG signal is offset, a time point that satisfies the offset state of the first EMG signal and the onset state of the second EMG signal may be detected as the walking assist starting point.

The torque calculator 260D may generate torques to apply to the driver 150 to assist muscular power of a user for a walking assist time based on the walking assist starting point. For example, the torque calculator 260D may calculate torques to be provided to the drivers 150 included in the hip joints 131 of the joint part 130. The magnitude of the torque to be provided to the driver 150 included in the right hip joint 131 and the torque to be provided to the driver 150 included in the left hip joint 131 may be proportional to the inclination of the body of the user with respect to the ground or the speed of the user. The torques to be provided to the drivers 150 included in the hip joints 131 may be in opposite directions.

Figure 11:
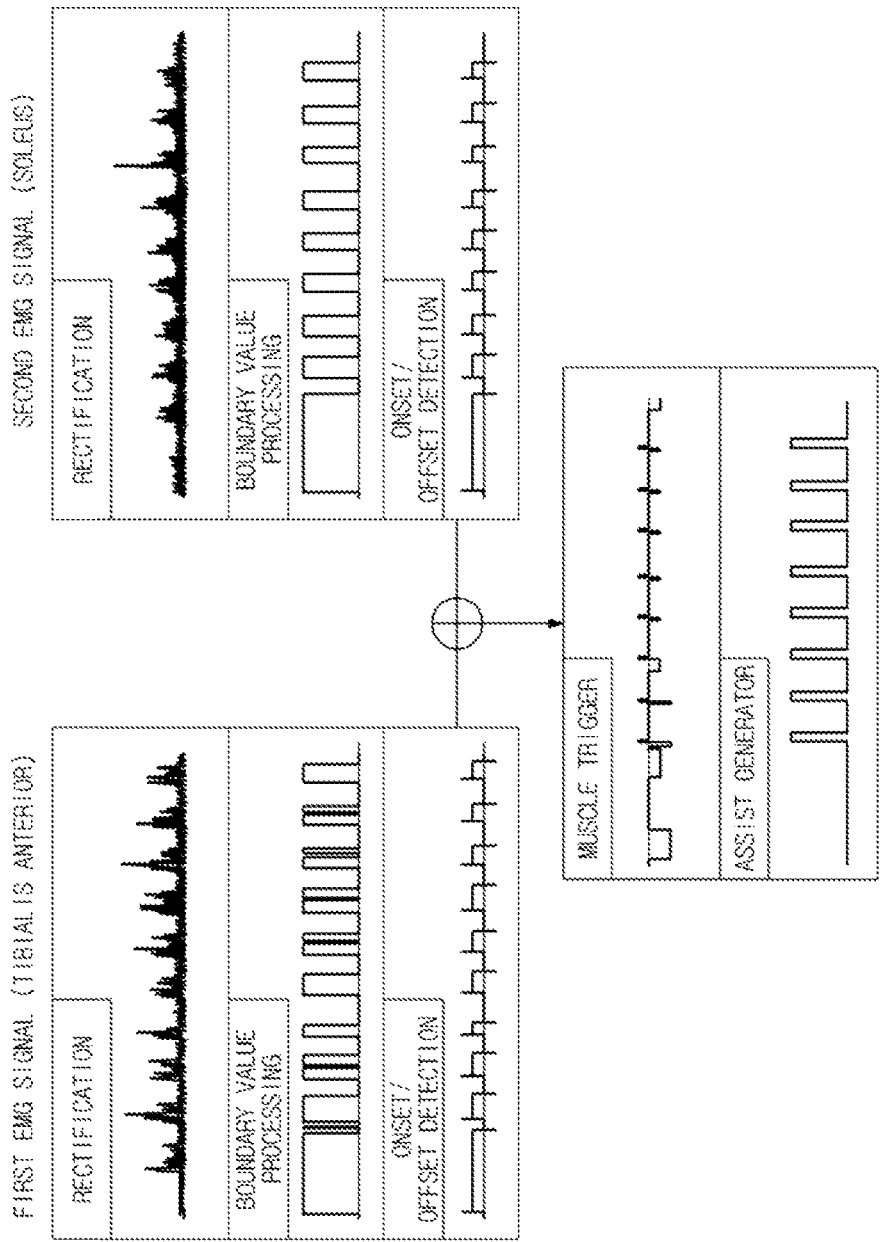
FIG. 11 is a view illustrating processing of first and second EMG signals measured at one leg of a user.

FIG. 11 is a view illustrating processing of first and second EMG signals measured at one leg of a user.

Referring to FIG. 11, the left part of FIG. 11 schematically illustrates processing of the first EMG signal, and the right part of FIG. 11 schematically illustrates processing of the second EMG signal. The first EMG signal is measured by the first EMG sensor 330 attached to the tibialis anterior, and the second EMG signal is measured by the second EMG sensor 340 attached to the soleus.

The waveforms of the first and second EMG signals are obtained by performing rectification, boundary value processing, and onset/offset detection on signals measured by the first and second EMG sensor 330, 340, respectively.

Referring to FIG. 11, it is noted that a time when the first EMG signal is offset and the second EMG signal is onset is detected as a walking assist starting point. Further, the controller 200 may utilize the gravitational acceleration measured by the wearable robot 1 when detecting the walking assist starting point.

Figure 12:
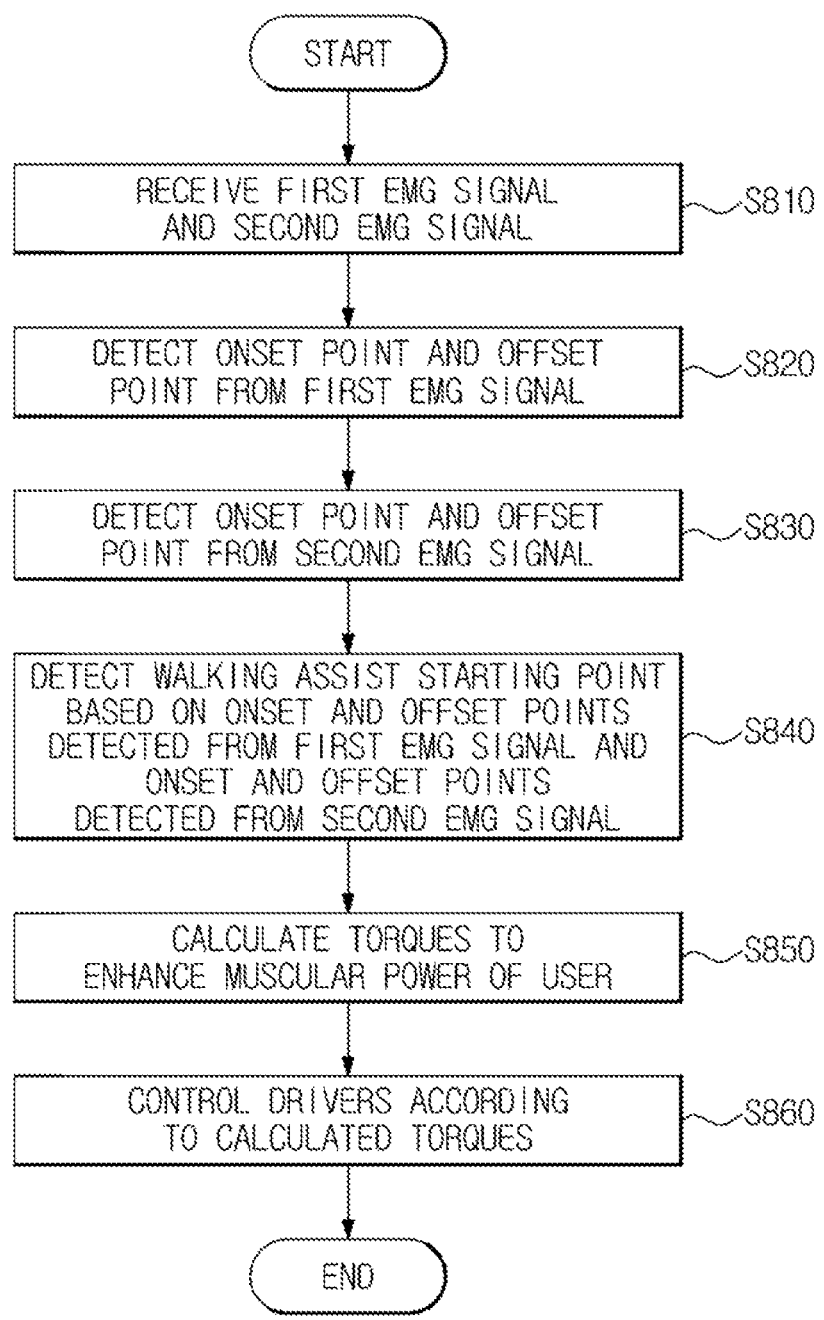
FIG. 12 is a flowchart of a method for controlling a wearable robot, according to some example embodiments.

FIG. 12 is a flowchart of a method for controlling the wearable robot 1, according to some example embodiments.

Referring to FIG. 12, in the method described below, it is assumed that, as in FIG. 1, the wearable robot 1 is worn on two legs of a user and that the first and second EMG sensors 330 and 340 are attached to each of the two legs of the user. However, example embodiments are not limited thereto. The first EMG sensor 330 is attached to the tibialis anterior of each leg, and the second EMG sensor 340 is attached to the soleus of each leg.

In operation S810, the controller 200 receives the first and second EMG signals respectively from the first and second EMG sensors 330 and 340. The first and second EMG signals may be detected by the first EMG sensor 330 may and the second EMG sensor 340, respectively. The first EMG signal detected by the first EMG sensor 330 may be amplified, rectified, filtered, and A/D converted before transmission to the controller 200. Likewise, the second EMG signal detected by the second EMG sensor 340 is amplified, rectified, filtered, and A/D converted before the transmission to the controller 200. Alternatively, the controller 200 may receive the raw signals from the first and second EMG sensors 330 and 340 and perform the amplification, rectification, filtration, and A/D conversion therein.

In operation S820, the controller 200 detects an onset point and an offset point from the first EMG signal. The controller 200 may detect the onset and offset point of the first EMG signal by performing boundary value processing on the first EMG signal, and detecting the onset and offset points from the first EMG signal on which boundary value processing is performed.

In operation S830 the controller 200 detects an onset point and an offset point from the second EMG signal. The controller 200 may detect the onset and offset point the second EMG signal by performing boundary value processing on the second EMG signal, and detecting the onset and offset points from the second EMG signal on which boundary value processing is performed.

In operation S840, the controller 200 detects a walking assist starting point based on the onset and offset points detected from the first EMG signal and the onset and offset points detected from the second EMG signal. According to some example embodiments, the controller 200 may detect the walking assist starting point by detecting a time when the first EMG signal is in an offset state and the second EMG signal in an onset state, as the walking assist starting point. According to other example embodiments, the controller 200 may also utilize the detection of whether the gravitational acceleration of the wearable robot 1 is rapidly increasing.

In operation S850, if the walking assist starting point is detected, the controller 200 calculates torques to enhance muscular power of the user. According to some example embodiments, the controller 200 may calculate the torques associated with the drivers 150 included in the hip joints 131 of the gear part 100, based on the inclination of the upper body of the user. For example, the calculated torques may be proportional to the inclination of the upper body of the user. According to other example embodiments, the controller 200 may calculate the associated with the drivers 150 included in the hip joints 131 of the gear part 100, based on the speed of the user. For example, the calculated torques may be proportional to the speed of the user.

In operation S860, the controller 200 may provide the calculated torques to the drivers 150 included in the hip joints 131 to enhance muscular power of the user who is walking. The controller 200 may provide a torque in a direction opposite to a walking direction of the user to the driver 150 included in the hip joint 131 of a leg at which the walking assist starting point is detected, and provide a torque in the walking direction of the user to the driver 150 included in the hip joint 131 of a leg opposite to the leg at which the walking assist starting point is detected.

In example embodiments, the controller 200 may include a processor and a memory (not shown).

The processor may be an arithmetic logic unit, a digital signal processor, a microcomputer, a field programmable array, a programmable logic unit, a microprocessor or any other device capable of responding to and executing instructions in a defined manner such that the processor is programmed with instructions that configure the processing device as a special purpose computer to perform the operations illustrated in FIG. 12, such that the controller 200 controls the drivers 150, such that the drivers 150 apply a torque to the hip joints 131 of the gear part 100, based on signals received from the sensors 300.

The instructions may be stored on a non-transitory computer readable medium. Examples of non-transitory computer-readable media include magnetic media such as hard disks, floppy disks, and magnetic tape; optical media such as CD ROM discs and DVDs; magneto-optical media such as optical discs; and hardware devices that are specially configured to store and perform program instructions, such as read-only memory (ROM), random access memory (RAM), flash memory, and the like. The non-transitory computer-readable media may also be a distributed network, so that the program instructions are stored and executed in a distributed fashion. The program instructions may be executed by one or more processors.

Further, in some example embodiments, some of the components of the wearable robot 1 may be implemented as a module. Here, the 'module' refers to a software-based component or a hardware component such as a field programmable gate array (FPGA) or an application specific integrated circuit (ASIC), and performs certain functions. However, the module is not limited to the software or hardware component. The module may be configured to be placed in an addressable storage medium, or to execute one or more processors.

For example, modules may include components such as software components, object-oriented software components, class components, and task components, processes, functions, attributes, procedures, subroutines, segments of program codes, drivers, firmware, microcodes, circuits, data, databases, data structures, tables, arrays, and variables. Functions provided by the components and modules may be combined into a smaller number of components and modules, or be separated into additional components and modules. Moreover, the components and modules may execute one or more CPUs in a device.

Some example embodiments may be implemented by a medium including computer-readable codes/instructions to control at least one processing element of the above-described embodiments, for example, a computer-readable medium. Such a medium may correspond to a medium/media which may store and/or transmit the computer-readable codes.

The computer-readable codes may be not only recorded in a medium but also transmitted over the Internet. For example, the medium may include a magnetic storage medium (for example, a ROM, a floppy disk, or a hard disk), an optical recording medium (for example, a CD-ROM or a DVD), or a transmission medium, such as a carrier wave. Further, the medium may be a non-transitory computer-readable medium. Since the medium may be a distributed network, the computer-readable code may be stored, transmitted and executed in a distributed manner. Further, for example, the processing element may include a processor or a computer processor, and be distributed and/or included in one device.

As is apparent from the above description, a walking assist starting point to assist a user with walking may be detected using EMG sensors without utilizing sensors such as a pressure sensor, force/torque sensor, encoder, and potentiometer.

Since the EMG sensors are attached to lower legs of the user, compared to a case that the EMG sensors are attached to upper legs of the user, user discomfort may be reduced.

Although a few example embodiments have been shown and described, it would be appreciated by those skilled in the art that changes may be made in these example embodiments without departing from the principles and spirit of the example embodiments, the scope of which is defined in the claims and their equivalents.

What is claimed is:

1. A wearable robot comprising:
   an assistance device having an exoskeleton structure configured to be worn on legs of a user;
   sensors including,
      a pair of first electromyogram (EMG) sensors and a pair of second EMG sensors, the pair of first EMG sensors configured to attach at a first location on respective legs of the user and to detect first EMG signals, the pair of second EMG sensors configured to attach at a second location on the respective legs and to detect second EMG signals, and
      an acceleration sensor configured to detect walking acceleration of the user; and
   a controller configured to,
      detect a start of a walking cycle in response to a rapid increase in the walking acceleration of the user,
      detect a first point when, after the rapid increase in the walking acceleration of the user, one of the first EMG signals associated with a first one of the legs is in an offset state and one of the second EMG signals associated with the first one of the legs is in an onset state, the onset state being a state when a muscle corresponding to one of the sensors on the legs of the user is activated and the offset state being a state when the muscle on the legs of the user is deactivated,
      set the first point as a walking assist starting point for the first one of the legs, the walking assist starting point being a point in the walking cycle in which the assistance device begins assisting the user with walking using the first one of the legs, and
      apply torque to a driver for a walking assistance duration of the first one of the legs by,
         instructing the driver to apply torque associated with the assistance device beginning at the walking assistance starting point,
         detecting a second point when one of the first EMG signals associated with a second one of the legs is in the onset state, the onset state being a state when the muscle on the second one of the legs of the user is activated, and
         instructing the driver to assist muscular power of the user for the walking assistance duration from the walking assist starting point until the second one of the legs of the user contact a ground.

2. The wearable robot according to claim 1, wherein
   the pair of first EMG sensors are configured to attach at the first location on the respective legs of the user corresponding to a location of a tibialis anterior muscle of the user, and
   the pair of second EMG sensors are configured to attach at the second location on the respective legs of the user corresponding to a location of a triceps surae muscle of the user.

3. The wearable robot according to claim 1, wherein the pair of second EMG sensors are configured to attach at the second location on the respective legs of the user corresponding to a location of a soleus muscle of the user.

4. The wearable robot according to claim 1, wherein the controller is configured to determine if an amplitude of each of the first and second EMG signals are above or below a boundary before determining the walking assist starting point.

5. The wearable robot according to claim 1, wherein the controller includes,
   a first filter configured to filter each of the first and second EMG signals before determining the walking assist starting point; and
   a second filter configured to filter each of the first and second EMG signals before determining the walking assist starting point, the second filter having a cutoff frequency different from a cutoff frequency associated with the first filter.

6. The wearable robot according to claim 5, wherein
   the first filter is a low pass filter (LPF), and
   the second filter has a cutoff frequency associated therewith that is lower than the cutoff frequency associated with the first filter.

7. The wearable robot according to claim 1, wherein the sensors further comprise: a gyro sensor configured to detect inclination of an upper body of the user.

8. The wearable robot according to claim 1, wherein the controller is configured to calculate the torque such that the torque is proportional to inclination of a body of the user or walking speed of the user.

9. The wearable robot according to claim 1, wherein the driver is a first driver associated with a first hip joint, and the wearable robot further comprises: a second driver associated with a second hip joint.

10. The wearable robot according to claim 9, wherein the controller is configured to,
    apply the torque to the first driver associated with the first one of the legs in a direction opposite to a walking direction of the user, and
    apply the torque to the second driver associated with the second one of the legs in the walking direction of the user.

11. A method for controlling a wearable robot, the wearable robot including an assistance device having an exoskeleton structure configured to be worn on legs of a user, the method comprising:
    receiving first electromyogram (EMG) signals and second EMG signals from a pair of first EMG sensors and a pair of second EMG sensors, respectively, the pair of first EMG sensors configured to attach at a first location of respective legs of the user, the pair of second EMG sensors configured to attach at a second location of the respective legs;
    receiving, from an acceleration sensor, acceleration information indicating a walking acceleration of the user;
    detecting a start of a walking cycle in response to a rapid increase in the walking acceleration of the user;

detecting, a first point when, after the rapid increase in the walking acceleration of the user, one of the first EMG signals associated with a first one of the legs is in an offset state and one of the second EMG signals associated with the first one of the legs is in an onset state, the onset state being a state when a muscle on the legs of the user is activated and the offset state being a state when the muscle on the legs of the user is deactivated;

setting the first point as a walking assist starting point, the walking assist starting point being a point in the walking cycle in which the assistance device begins assisting the user with walking using the first one of the legs; and applying torque to a driver for a walking assistance duration of the first one of the legs by,
instructing the driver to apply torque associated with the assistance device beginning at the walking assistance starting point,
detecting a second point when one of the first EMG signals associated with a second one of the legs is in the onset state, the onset state being a state when the muscle on the second one of the legs of the user is activated, and
instructing the driver to assist muscular power of the user for the walking assist duration from the walking assist starting point until the second one of the legs of the user contact a ground.

12. The method according to claim 11, wherein
the first pair of EMG sensors are configured to attach at the first location on the respective legs of the user corresponding to a location of a tibialis anterior muscle of the user, and
the second pair of EMG sensors are configured to attach at the second location on the respective legs of the user corresponding to a location of a soleus muscle of the user.

13. The method according to claim 11, wherein the driver is a first driver associated with a first hip joint, and the wearable robot further comprises: a second driver associated with a second hip joint.

14. The method according to claim 13, wherein the applying the torque comprises:
applying the torque to the first driver associated with the first one of the legs in a direction opposite to a walking direction of the user; and
applying the torque to the second driver associated with the second one of the legs in the walking direction of the user.

* * * * *